United States Patent [19]

Tomlin

[11] Patent Number: 4,740,473
[45] Date of Patent: Apr. 26, 1988

[54] SODIUM SULFIDE ANALYZER

[75] Inventor: Robert L. Tomlin, Waldron, Ark.

[73] Assignee: Sampling Technology, Inc., Waldron, Ark.

[21] Appl. No.: 934,913

[22] Filed: Nov. 25, 1986

[51] Int. Cl.⁴ .................... G01N 31/00; G01N 33/00; G01N 35/00

[52] U.S. Cl. ........................................ 436/79; 422/62; 422/81; 422/82; 422/260; 423/561 A; 423/563; 436/52; 436/55; 436/119; 436/120

[58] Field of Search ................. 422/62, 68, 81, 82, 422/260; 436/47, 48, 52, 55, 119, 120, 79; 423/561 A, 563, 571, 572

[56] References Cited

U.S. PATENT DOCUMENTS

| | | |
|---|---|---|
| 3,712,795 | 1/1973 | Hamshere et al. . |
| 3,819,817 | 6/1974 | Van Slyke .............................. 423/563 |
| 4,026,667 | 5/1977 | Logan . |
| 4,174,202 | 11/1979 | Simpson . |
| 4,402,910 | 9/1983 | Smith et al. . |

FOREIGN PATENT DOCUMENTS

| | | |
|---|---|---|
| 0053886 | 5/1976 | Japan . |
| 0047759 | 4/1981 | Japan . |
| 84/04597 | 11/1984 | World Int. Prop. O. ............ 436/79 |

*Primary Examiner*—Barry S. Richman
*Assistant Examiner*—Robert J. Hill, Jr.
*Attorney, Agent, or Firm*—Dennison, Meserole, Pollack & Scheiner

[57] ABSTRACT

The invention provides a method and apparatus for measuring the sodium sulfide content of liquid industrial process streams. According to this method, a sample of the liquid is passed through a heated filter to remove solids and reduce viscosity and a portion of the sample is then mixed with carbon dioxide to generate hydrogen sulfide gas. The hydrogen sulfide gas is separated from the reacted liquid sample, and a portion of the gas is mixed with dilution air and then analyzed quantitively for hydrogen sulfide.

15 Claims, 3 Drawing Sheets

SODIUM SULFIDE ANALYZER

BACKGROUND OF THE INVENTION

The present invention relates to a process and apparatus for measuring the sodium sulfide content of liquid industrial process streams, in which a sample is extracted from a process stream, and reacted with a gas to produce hydrogen sulfide, which is measured as an indication of the sodium sulfide content of the process stream.

Many industrial processes can benefit from the continuous measurement of the sodium sulfide concentration in digester cooking liquors and gas scrubbing solutions. At this time, sodium sulfide, $Na_2S$ concentrations are determined by transporting a sample of the alkaline solution to a laboratory and analyzing the sample by potentiometric titration or by acidification, purging and trapping the resulting gases. Due to the corrosive nature of the highly alkaline solutions and the high solids content, continuous on-line analysis for sodium sulfide has not been achieved.

In the past, continuous sulfide measurement has been attempted, using specific ion electrodes or oxidation-reduction electrodes. These methods have not proven successful due to the high maintenance necessary to achieve continuous operation. The specific ion electrodes are prone to leakage and contamination and give a variablr output depending upon the temperature and pH of the alkaline solution being tested. The oxidation-reduction electrodes have shown a lack of reliability due to contamination of the electrodes. Oxidation-reduction electrodes also are only useful for the lower $Na_2S$ concentrations because of the limited output of the detector at the higher $Na_2S$ concentrations. While the normal range of $Na_2S$ concentrations to be measured is 40 grams/liter down to 0.01 grams/liter, the metal, oxidation-reduction electrodes are useful only at concentrations of 1 gram/liter or less.

Of the laboratory tests currently used to measure the sodium sulfide content of alkaline solutions, it is felt that the method that acidifies the solution to convert the sodium sulfide to $H_2S$ and then measure the resulting $H_2S$ is the most useful approach. This measurement method closely approaches the reactions that occur in combustion processes and should give a measurement of sodium sulfide that will relate more closely to the sulfur gases emitted to the atmosphere.

SUMMARY OF THE INVENTION

The sodium sulfide analyzer of the invention has been developed to give a continuous on-line signal that relates to the $Na_2S$ concentration of the alkaline solution. The $Na_2S$ concentration in the alkaline solution is determined by extracting a portion of the process stream, injecting a controlled flow of carbon dioxide to convert $Na_2S$ to $H_2S$ and then measuring the resulting $H_2S$ with an $H_2S$ detector. The $H_2S$ measured in this manner directly relates to the $Na_2S$ concentration of the process stream. The sodium sulfide to hydrogen sulfide reaction is described by the following equation:

$$Na_2S + H_2O + CO_2 \rightarrow Na_2CO_3 + H_2S$$

The apparatus of the invention includes means to extract a portion of a process stream, means to condition the sample prior to reaction, a reaction chamber, means to extract the resulting $H_2S$ from the alkaline solution, a gas dilution system to establish the concentration and quality of gas going to the $H_2S$ detector and an $H_2S$ detector.

DESCRIPTION OF THE PREFERRED EMBODIMENTS

Figure 1:
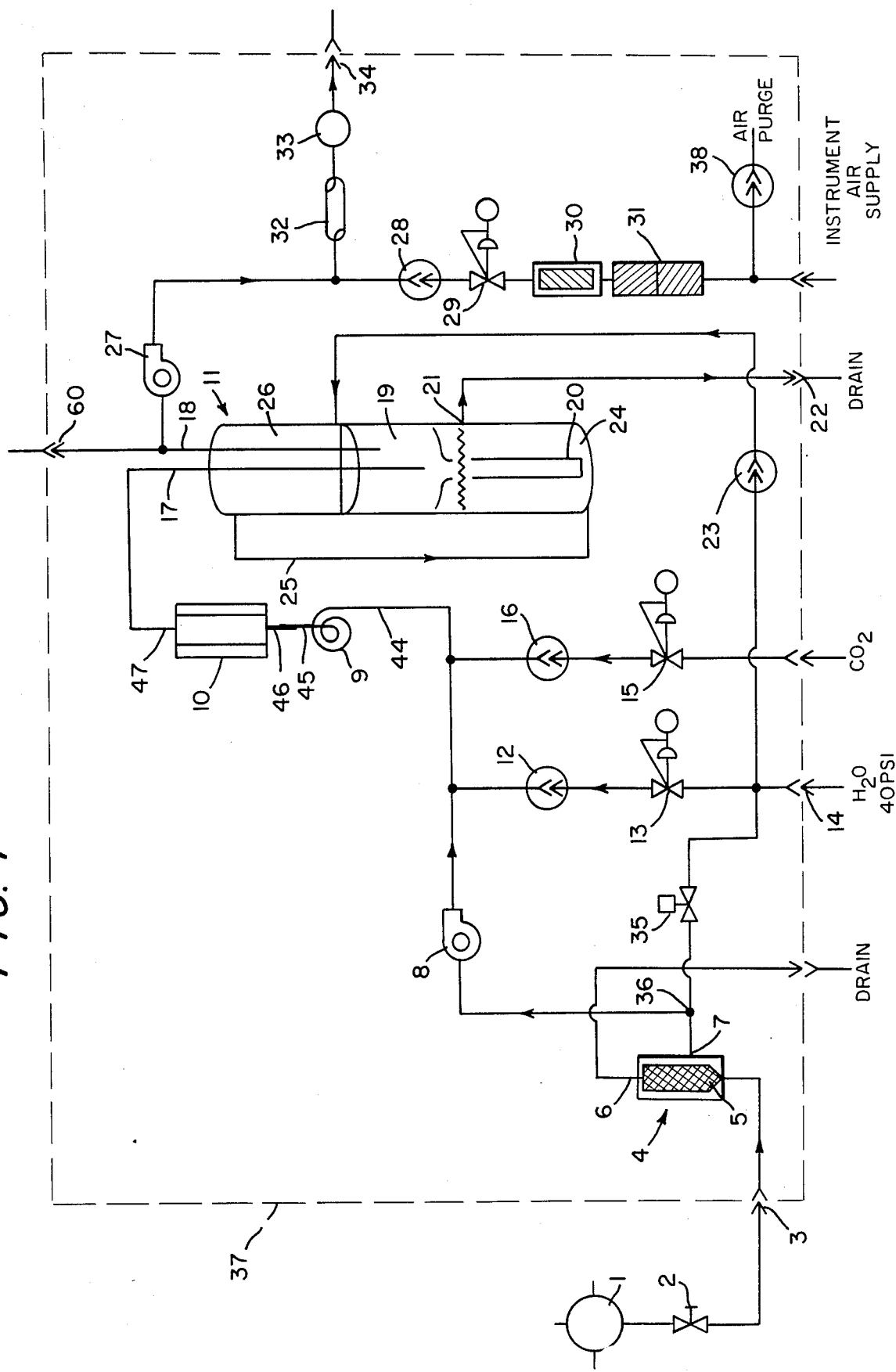
FIG. 1 is a schematic diagram of the apparatus according to the invention.

All components for the Sodium Sulfide Analyzer are enclosed within a 24 inch (H)×24 inch (W)×8 inch (D) Nema 4 fiberglass enclosure 37, in FIG. 1. The enclosure, which is designed to be installed near the process sampling point, is air purged from vent 38 and temperature controlled to give reliable and stable output in severe process environments, by a heating means, not shown. Typically, the enclosure is maintained slightly above ambient temperature, in a range of about 104°–113° F. (40°–45° C.). Maintenance of a constant temperature is important for reliable operation. The analyzer requires a source of electricity, pressurized water, pressurized air, a cylinder of $CO_2$, and a liquid drain at the installation site. The analyzer as described will operate satisfactorily in an environment between −5 and 110 degrees F.

Figure 2:
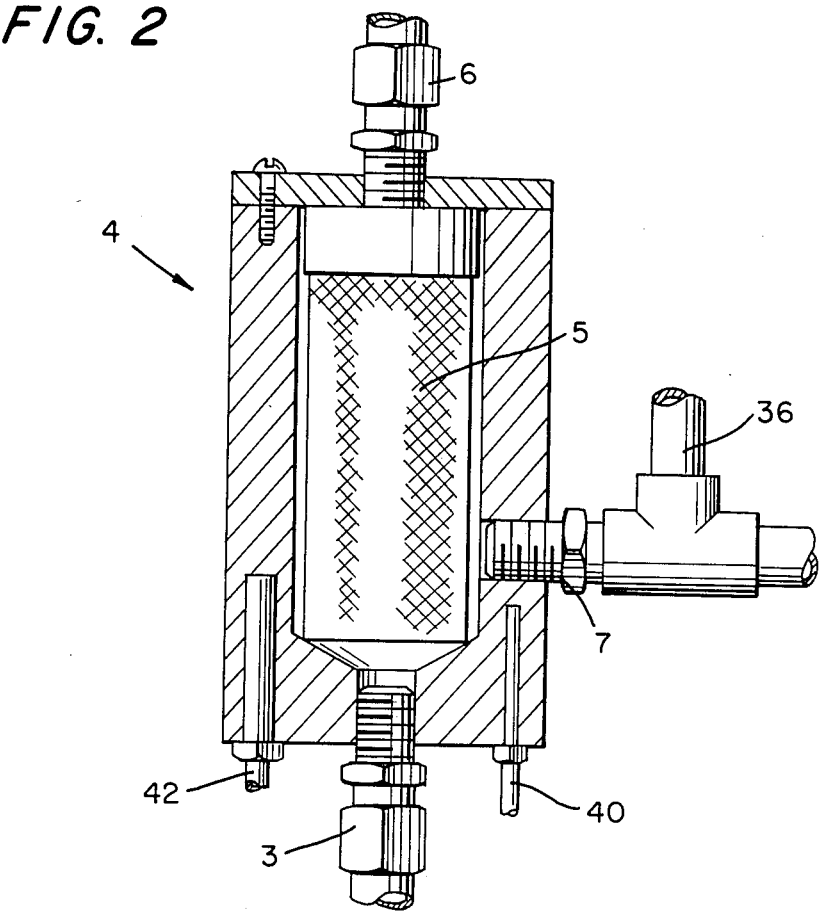
FIG. 2 is a cross-sectional view of a heated filter according to the invention.

In normal operation of the system, a sample of the process stream is allowed to flow from process line 1 through a throttle valve 2. This flowrate is not critical; any flowrate between 5 cc/min and 1 liter/min is acceptable. The sample enters the $Na_2S$ analyzer at port 3, from which the sample flows to heated filter 4, shown in cross section in FIG. 2. Filter 4 is heated to ensure a constant viscosity sample to the metering pump 8. The heated filter 4 is heated to approximately 180 degrees F, although slightly higher or lower temperatures, for example, 110°–220° F., may be required for certain process streams. The filter temperature is controlled by a solid state proportional temperature controller 40 and cartridge heater element 42.

The heated filter includes an outlet port 7 which serves as a manifold from which a metering pump 8 can pull a precise flow rate at a constant inlet pressure. The heated filter 4 contains a stainless steel filter screen 5 to remove solids that may interfere with the pumping accuracy of metering pump 8.

Another filter outlet 6 is connected to a drain for draining excess liquid, and to ensure that the metering pump 8 will always receive a sample at essentially atmospheric pressure.

Metering pump 8 extracts a small portion of sample from heated filter 4 and delivers this sample to a mixing chamber 9 and reaction chamber 10. The flow stability of metering pump 8 is very important to the overall stability of the $Na_2S$ analyzer output; the metering pump 8 is generally an all ceramic piston type pump, such as is available from F.M.I. under the designation RPG201CKCW. The pump utilizes a rotating piston which serves as both the piston and the inlet and outlet valves for the pump. The flowrate from the pump is adjustable by changing the piston stroke length. Flowrate stability of the pump is improved by maintaining a constant pressure at pump inlet and outlet.

Pump inlet pressure is controlled by the open manifold design of the heated filter 4 and outlet pressure is controlled by the low restriction design of mixing chamber 9, reaction chamber 10, and a gas separator 11. The metering pump delivers a flowrate of 2 to 5 cc/min. Other flowrates, for example, 1 to 20 cc/min., are possible and may be desirable for certain applications.

Figure 3:
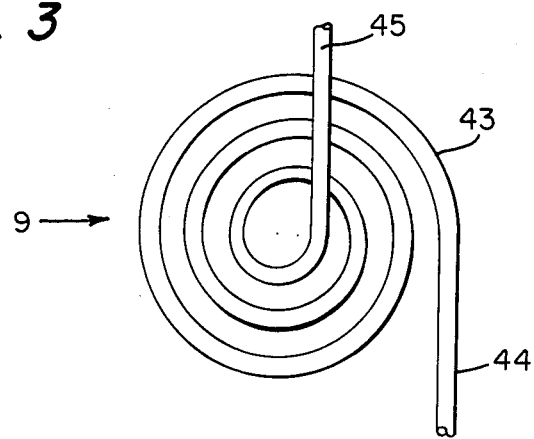
FIG. 3 is a front view of a mixing chamber according to the invention.

At the output of metering pump 8 the sample is diluted with water from flow orifice 12. Pressure regulator 13 controls the head pressure to water flow control orifice 12. The water flowrate is set to approximately 5 times the flowrate from metering pump 8, but this can vary within a range of, for example, 3:1 to 7:1. The sample viscosity is lowered with water to aid the reaction between the sample and $CO_2$ and to prevent plugging and scale formation in the reaction chamber. After the sample is diluted with water, an acidic gas, typically carbon dioxide, is injected into the sample stream. The $CO_2$ flowrate is controlled at approximately 100 times the metering pump 8 flowrate, which ensures adequate $CO_2$ for complete reaction with the sodium sulfide in the sample stream. The $CO_2$ flowrate is controlled at approximately 100 times the metering pump 8 flowrate, which ensures adequate $CO_2$ for complete reaction with the sodium sulfide in the sample stream. The $CO_2$ flowrate is controlled by a pressure regulator 15 and a flow control orifice 16. After diluting the sample with water and injecting $CO_2$, the sample is routed to mixing chamber 9 shown in a front view in FIG. 3. Mixing chamber 9 is designed to aggressively mix the sample, water, and $CO_2$. The mixing chamber 9 includes approximately 6 feet of Teflon tubing 43 in a coiled configuration, for example, ¼" O.D. tubing in a coil 4" in diameter, with inlet 44 and outlet 45. The high flowrate of the $CO_2$ relative to the sample flowrate causes a vigorous stirring of the sample mixture in the mixing chamber.

Figure 4:
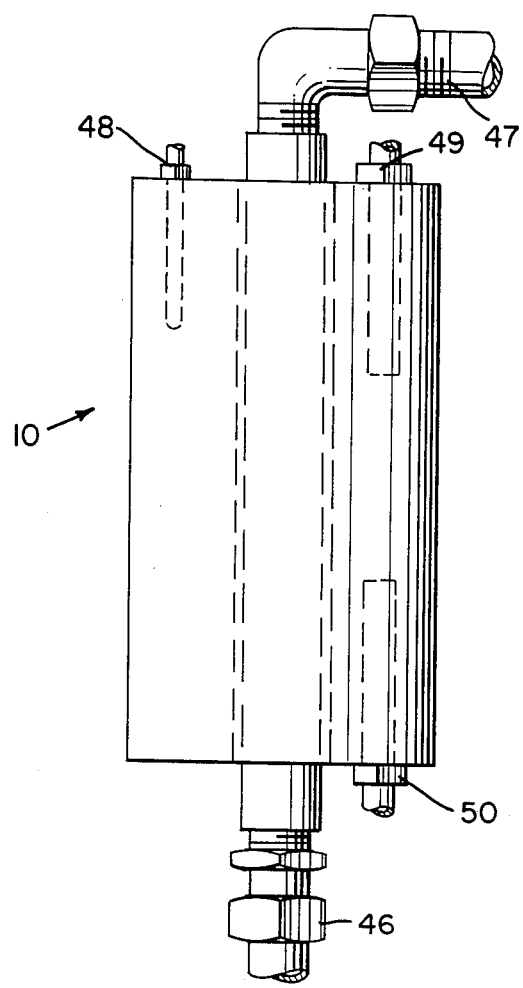
FIG. 4 is a cross-sectional view of a reaction chamber according to the invention.

From the mixing chamber 9, the partially reacted sample is routed to the heated reaction chamber 10, shown in cross section in FIG. 4. The reaction chamber includes a stainless steel tube approximately 8 inches long × 0.5 inches I.D. with inlet 46 and outlet 47. The reaction chamber block, and thus the reaction chamber, is temperature controlled by a solid state proportional temperature controller 48 and heaters 49 and 50 to 235 degrees F. Slightly higher or lower temperatures, for example, 180° F. to 300° F., may be required for specific applications.

The design of the reaction chamber causes bubbles to be formed in the reaction chamber, which allows for maximum surface exposure between the diluted sample and the injected $CO_2$. The sample bubbles form and break many times before exiting the reaction chamber. The combination of elevated temperature and complete mixing of the process sample and the $CO_2$ causes a highly efficient and stable reaction to take place.

From the reaction chamber 10, the reacted sample and the evolved $H_2S$ are routed to the gas separator 11, which functions to separate the evolved $H_2S$ from the reacted sample, continuously drain the reacted sample, dilute the reacted and higher viscosity sample for ease in draining and lower maintenance, and to form a gas seal between the water drain port and the gas outlet port of gas separator 11. The gas separator consists of a Pyrex glass heat exchanger formed from tubes 17 and 18 passing through a chamber 26 to a chamber 19, and a liquid seal section including chamber 24 and tube 25, attached to the bottom of the heat exchanger.

A water flow of approximately 1 liter per minute from orifice 23 to upper cooling chamber 26 is used to cool the upper part of heat exchanger tubes 17 and 18 passing through upper chamber 26. This water flow is then routed to the bottom chamber 24 via tube 25. Water in the bottom chamber rises to the level of outlet port 21 from which it flows to drain 22.

The reacted sample enters tube 17 and the liquid sample and evolved $H_2S$ gas are cooled by water flow around exchanger tube 17. At the bottom of tube 17, the reacted sample drops into tube 20 and the gas escapes into gas separation chamber 19. The $H_2S$ in chamber 19 flows to vent 60 through upflowing heat exchanger tube 18. The evolved $H_2S$ is cooled in exchanger tube 18 as its passes through chamber 26, to further reduce the water content of the outlet gas stream.

Liquid condensed from tube 17 and tube 18 flow, along with reacted sample, into tube 20 which is open at the bottom to allow the liquid to drain into chamber 24, and then through port 21 to liquid drain 22. Tube 20 and liquid filled chamber 24 provide a liquid gas seal that minimizes the contact between the evolved $H_2S$ and the water used for the gas seal. The liquid in chamber 24 is constantly replenished by outlet tube 25.

Figure 5:
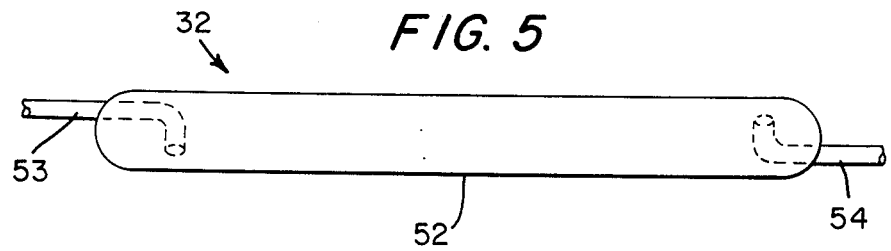
FIG. 5 is a cross-sectional view of a second mixing chamber according to the invention.

With sodium sulfide concentrations ranging between 0.01 g/l and 40 g/l, the concentration of $H_2S$ at vent 26 will range between 10 ppm and 40,000 ppm $H_2S$ in a balance gas of $CO_2$. The gas exiting vent 26 will have a dewpoint between 40 and 80 degrees F. To accomplish the wide range requirement (10 ppm to 40,000 ppm) and ensure long $H_2S$ detector cell life, the gas exiting tube 18 is diluted with sulfur-free air prior to introduction to the $H_2S$ detector. Dilution air is provided by a supply system including flow control orifice 28, pressure regulator 29, particulate filter 30, and sulfur scrubbing filter 31. A metering pump 27 supplies a quantity of the $H_2S$ containing gas; this pump can be of the same type as metering pump 8, except that metering pump 27 uses a ceramic piston and a carbon piston liner to accommodate pumping a dry gas sample. A suitable pump is available from F.M.I. under the designation RPG4001CKY. The dilution ratio is changed by varying the metering pump speed, metering pump stroke length, or flow control orifice 28. The $H_2S$-containing gas and air are supplied to mixing chamber 32, shown in cross section in FIG. 5, which ensures complete mixing of the air from orifice 28 and the flow from metering pump 27. Mixing chamber 32 is a 4" long Pyrex glass tube 52 having inlet tubing 53 and outlet tubing 54. Metering pump 27 flow rates may be set between 0.1 and 400 cc/min. Dilution air flow rates through orifice 28 may vary between 0.1 and 10 cc/min.

An electrochemical $H_2S$ detector 33 is provided, although any type $H_2S$ detector may be used which demonstrates reliable performance on gases with high $CO_2$ background concentrations. The $H_2S$ detector is selected to accommodate the lowest desired range. A commercially available detector may be obtained from Texas Analytical Controls Inc., under the designation P/N 301XM. Higher ranges are accomplished by diluting the sample gas with air until the gas concentration is within the range of the $H_2S$ detector.

To ensure reliable functioning of heated filter 4, filter screen 5 must be periodically backflushed with water to clean the filter screen. Back purge valve 35 is used to supply high pressure water to heated filter 4. Introducing backpurge water at connection 36 allows backflushing the filter screen 5 without interrupting the process flow. The back purge water flows to drain 6 along with the process sample flow.

The sodium sulfide analyzer is calibrated by analyzing, by conventional lab techniques, a sample collected from drain port 6 and then adjusting the H₂S detector output to the value determined in the laboratory test. Calibration should be accomplished as often as required to meet process control needs. A weekly calibration should be adequate to meet most process accuracy requirements.

EXAMPLE

The sodium sulfide analyzer of the invention is used for analysis in a black liquor oxidation system for a kraft pulp mill.

A black liquor oxidation system is used to oxidize the sodium sulfide in black liquor to sodium thiosulfate or sodium sulfate. Oxidizing the black liquor prior to burning in the recovery boiler greatly reduces hydrogen sulfide emissions from the recovery boiler stack. If the black liquor is over-oxidized, the BTU value of the black liquor is reduced and the viscosity of the black liquor is increased, causing handling problems. If the black liquor is under oxidized, the hydrogen sulfide emissions from the recovery boiler will be excessive. The oxidation state of the black liquor is controlled by controlling the air or oxygen flowrate through a black liquour reactor.

The sodium sulfide analyzer according to the invention monitors the sodium sulfide concentration at the outlet of the black liquor reactor tank. The analyzer enclosure is maintained at a temperature of about 113° F. (45° C.). A flowrate of about 200 cc/min. is maintained through heated filter 4 with metering pump 8 withdrawing about 2.4 cc/min. for analysis. The remainder of the black liquor flows through outlet 6 to the drain. The heated filter is maintained at a temperature of about 180° F. (82° C.).

The analysis sample withdrawn by metering pump 8 is mixed with water at a flowrate of about 12 cc/min. and carbon dioxide at a flowrate of about 400 cc/min., and is passed to mixing chamber 9, and then reaction chamber 10 which is maintained at a temperature of about 235° F. (113° C.). The mixed sample is then passed to the gas separator 11 where water flow of approximately 1 liter per minute at upper chamber 26 is used to cool the sample entering through tube 17. Gas is withdrawn from the gas separator by metering pump 27 at a rate of about 100 cc/min., is diluted with air flowing at a rate of 2.5 liters per minute, and is passed to the mixing chamber 32. The hydrogen sulfide detector 33 is set for a range of about 40 ppm.

The output signal from the sodium sulfide analyzer may be sent to a strip chart recorder or other display device, or be used for manual control of the oxidation rate. If desired, the output signal from the analyzer may be connected to the air or oxygen flow controlling device of the black liquor oxidation system, to achieve automatic control of the oxidation process.

What is claimed is:

1. A method for measuring the sodium sulfide content of a liquid industrial process stream comprising the steps of:
   a. removing a liquid sample from a liquid industrial process stream;
   b. elevating the temperature of said sample to reduce its viscosity;
   c. filtering said sample to obtain a filtered sample;
   d. extracting at least a portion of said filtered sample with a metering pump to obtain an extracted sample;
   e. thoroughly mixing and reacting said extracted sample with carbon dioxide gas to convert all sodium sulfide present in said extracted sample to hydrogen sulfide gas;
   f. separating any hydrogen sulfide gas produced in step e. from said extracted sample;
   g. extracting a portion of any separated hydrogen sulfide gas with a metering pump and mixing a desired quantity of air therewith to produce a mixture; and
   h. analyzing said mixture to quantitatively determine its hydrogen sulfide content as a measure of the sodium sulfide content of the liquid industrial process stream.

2. The method according to claim 1, wherein the extracted sample and any hydrogen sulfide gas produced in step e. are cooled during step f.

3. The method according to claim 1, wherein said extracted sample is diluted with water prior to being mixed and reacted with said carbon dioxide gas.

4. The method according to claim 1, wherein said extracted sample and said carbon dioxide gas are mixed thoroughly by simultaneously passing said extracted sample and said carbon dioxide gas through at least one mixing chamber.

5. The method according to claim 1, wherein the liquid sample is removed from the liquid industrial process stream at a rate of between 0.005 and 1 liter per minute.

6. The method according to claim 1, wherein the temperature of said liquid sample is elevated to about 110-220 F. in step b. to reduce its viscosity.

7. The method according to claim 1, wherein said extracted sample is extracted from said filtered sample by said metering pump at a flowrate of about 2 to 5 cc per minute.

8. The method according to claim 1, wherein said extracted sample and said carbon dioxide gas are reacted at a temperature of about 180-300 F.

9. An apparatus for measuring the sodium sulfide content of a liquid industrial process stream comprising:
   a. removing means for removing a liquid sample from a liquid industrial process stream;
   b. heated filter means operatively connected to said removing means for removing solids from and reducing the viscosity of a liquid sample received from said removing means;
   c. metering pump means operatively connected to said heated filter means for extracting a portion of a filtered sample received from said heated filter means to obtain an extracted sample;
   d. a source of carbon dioxide;
   e. first mixing means operatively connected to said metering pump means and said source of carbon dioxide for mixing an extracted sample received from said metering pump means and carbon dioxide received from said source of carbon dioxide and allowing them to react to convert all sodium sulfide in such an extracted sample to hydrogen sulfide gas;
   f. separation means operatively connected to said first mixing means for separating hydrogen sulfide gas from an extracted sample in a mixture received from said first mixing means;
g. pump means operatively connected to said separation means for extracting a portion of hydrogen sulfide gas received from said separation means;
h. a source of dilution air;
i. second mixing means operatively connected to said pump means and said source of dilution air for mixing an extracted portion of hydrogen sulfide received from said pump means and dilution air received from said source of dilution air;
j. measuring means operatively connected to said second mixing means for quantitatively measuring the hydrogen sulfide content of a mixture of dilution air and hydrogen sulfide gas received from said second mixing means.

10. The apparatus according to claim 9, wherein said first mixing means includes means defining a heated reaction chamber.

11. The apparatus according to claim 9, further comprising diluting means operatively connected between said metering pump means and said first mixing means for diluting an extracted sample received form said metering pump means before it is received by said first mixing means.

12. The apparatus according to claim 9, further comprising backflusing means operatively connected to said heated filter means for selectively backflushing said heated filter means with water.

13. The apparatus according to claim 9, wherein said heated filter means includes means defining a liquid inlet connected to said removing means, means defining a first outlet connected to said metering pump means, and means defining a second liquid outlet connected to a drain.

14. The apparatus according to claim 9, wherein said first mixing means includes tubing having two ends and being in a coiled configuration, said tubing comprising means defining an inlet at one end and means defining an outlet at the other end.

15. The apparatus according to claim 9, wherein said separation means includes:
a. means defining a cooling chamber having a inlet tube and a outlet tube extending therethrough;
b. means defining a gas separating chamber below said cooling chamber and having said inlet tube and said outlet tube opening therein and a liquid drainage tube extending downwardly therefrom;
c. means defining a liquid seal chamber below said gas separating chamber and having said liquid drainage tube opening therein and including means defining an outlet port for liquid; and
d. means for supplying cooling water to said cooling chamber and means for removing cooling water from said cooling chamber to said liquid seal chamber.

* * * * *